United States Patent [19]

Nesbitt et al.

[11] Patent Number: 4,487,759

[45] Date of Patent: Dec. 11, 1984

[54] TERTIARY AMINE STABILIZED MICRO-ENCAPSULATED COMPOSITIONS CONTAINING BEHAVIOR MODIFYING COMPOUNDS

[75] Inventors: Brenda F. Nesbitt, Weybridge; David R. Hall, Streatham; Ralph Lester, Heddon-on-the-Wall; Gordon J. Marrs, Maidenhead, all of England

[73] Assignees: Imperial Chemical Industries Limited; National Research Development Corporation, both of London, England

[21] Appl. No.: 240,990

[22] Filed: Mar. 5, 1981

[30] Foreign Application Priority Data

May 5, 1980 [GB] United Kingdom ............... 8007581

[51] Int. Cl.$^3$ ..................... A61K 9/50; A61K 35/64; A01N 25/28
[52] U.S. Cl. ...................................... 424/32; 424/33; 424/84
[58] Field of Search ............................ 424/32, 33, 84

[56] References Cited

PUBLICATIONS

Marks, R. J., Nesbitt, B. F., Hall, D. R., Lester, R., Bull. ent. Res. 68: 11–29, (1978) cited in Micro-Caps.
Marks, R. J., D. R. Hall, R. Lester, B. F. Nesbitt, M. Camburt, Bull. ent. Res. 71: 403–418, (1981).
Newmark et al., J. Econ. Entomol. 65(6): 1709–1711, (1972).
Wolf et al., J. Econ. Entomol. 65(4): 1039–1041, (1972).
Caro et al., Environmental Entomology 6(6): 877–881, (1977), Micro-Caps.

Kochansky et al., J. Chem. Ecology 3(4): 419–427, (1977) Pheromoney.
WO81/02505, Sep. 17, 1981, PCT Nesbitt et al., (45 pp.).

*Primary Examiner*—Shep K. Rose
*Attorney, Agent, or Firm*—Fred S. Whisenhunt

[57] ABSTRACT

Compositions containing insect behavior modifying compounds containing carbon-to-carbon unsaturation, e.g. pheromones, are stabilized by the addition of a tertiary phenylene diamine of formula:

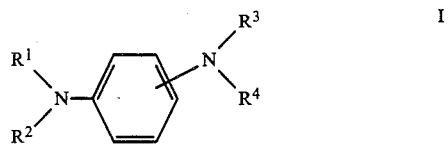

wherein $R^1$ represents an aromatic residue, $R^2$ represents H or an alkyl, alkenyl, cycloalkyl, cycloalkylalkyl, alkaryl, aralkyl, aryl, acyl, acyloxy or nitroso group and $R^3$ and $R^4$, which may be the same or different, each represents an alkyl, alkenyl, cycloalkyl, cycloalkylalkyl, alkaryl, aralkyl, aryl, acyl, acyloxy or nitroso group.

These compositions are usefully enclosed in micro-capsules for spraying in an area of insect infestation in order to disrupt mating patterns, and the invention particularly applies to micro-encapsulation of the compositions in polyureas, the tertiary phenylene diamines having the advantage that they do not react with the diisocyanate monomer during the micro-encapsulation process.

13 Claims, No Drawings

TERTIARY AMINE STABILIZED MICRO-ENCAPSULATED COMPOSITIONS CONTAINING BEHAVIOR MODIFYING COMPOUNDS

This invention relates to behaviour modifying compounds and is particularly concerned with the stabilisation of photodegradeable compounds of this type.

Some of the most potent behaviour modifying compounds known to man are the so-called pheromones. These may be defined as compounds which are secreted by one member of an animal species which can influence the behaviour or development of another member of the same animal species. Considerable study has been made of pheromones secreted by various insect species, the term "insect" being used here in its broad popular sense. More particularly, the pheromones of various species of moth have been investigated and these have been found to be long chain aliphatic alcohols, esters or aldehydes containing one or more sites of carbon to carbon unsaturation. The compounds are particularly potent in that extremely small quantities of these pheromones are able to bring about the behavioural modification in another member of that species over prolonged distances.

It is frequently found that these pheromones are secreted by members of one sex of the insect species and are able to influence the behaviour of members of the opposite sex of that species and that the pheromones can consequently be involved in the identification of members of the opposite sex of the species over prolonged distances. Many pheromone studies have been made in relation to insect species where, usually at the larval stage of development, the species acts as a pest on agricultural crops so that, in principle, the pheromone's property can be used as a method of insect control by controlling mating of the species.

Pheromones can therefore be used to bait traps during the mating season of the selected species by utilising an attractant pheromone (or a synthetic analogue thereof which mimics the activity of an attractant pheromone), to lure, usually the male, into the trap during the mating season and so prevent mating. More importantly, mating can be prevented by permeating the atmosphere with the sex pheromone or one of its components or synthetic analogues thereof, thus preventing male and female insects from locating one another. Consequently, subsequent damage to the crop by infestation at the larval stage can be minimised.

The practical implementation of pheromones in the field for insect control has not been entirely straightforward because usually, the naturally occurring pheromones, and synthetic analogues thereof, include one or more sites of carbon to carbon unsaturation which normally means that the compounds are highly susceptible to photodegradation. This means that while the full potency of the pheromone is exhibited initially, the potency is rapidly lost after exposure to sunlight.

One method which has been successfully used for the stabilisation of photodegradeable compounds, which are to be used agriculturally, is micro-encapsulation. Micro-encapsulation techniques are now well developed and enable photodegreadable biologically active compounds, including pheromones, to be contained within the walls of the micro-capsules which are prepared of an appropriate polymeric compound. The micro-capsules are usually spherical capsules having a diameter in the range of about 1 to 100 microns and the product frequently takes the form of a suspension of micro-capsules in a continuous aqueous phase so that the suspension can be supplied e.g. by spraying, to the locus to be protected.

The micro-encapsulation of biologically active compounds, including pheromones, has been recognised to give rise to many advantages, for example the microcapsule affords a certain measure of physical protection for the biologically active substance and permits a uniform coverage of the locus to be protected by, for example, spraying the micro-encapsulated product to give a surface coating on the locus from which there will be a slow release of biologically active compound over a prolonged period of time.

Various polymeric materials have been proposed for the production of the micro-capsules including polyamides, polyesters, polycarbonates, polyureas, polyurethanes and gelatine.

Of these, polyureas have proved to be particularly suitable as they can be readily generated, for example, by a polycondensation between a polyisocyanate and polyamine. One particular way to micro-encapsulate products of this type which are immiscible with water is to emulsify the biologically active compound in an aqueous medium together with a polyisocyanate such as toluene diisocyanate and then to introduce a polyamine such as ethylene diamine whilst vigorously stirring the mixture so that a polyurea forming reaction occurs forming microcapsules which enclose the biologically active component and any other materials to be formulated with the biologically active component.

Such techniques have previously been used for biologically active compounds but unfortunately, it has been found that where the biologically active compound is photodegradeable, e.g. as is the case with an unsaturated pheromone, the microcapsule is unable to protect fully the biologically active compound against the influence of sunlight and consequently, degradation with consequent loss of biological activity rapidly occurs.

It has been proposed to formulate photodegradeable biologically active compounds with stabilisers, such as polyamines, which are very effective in protecting the biologically active compound against photodegradation but unfortunately, it is not practical to utilise the polyamines hitherto used for stabilisation in cases where it is desired to present the biologically active material in micro-encapsulated form in a polyurea. This is because the polyamines used hitherto have been primary or secondary polyamines which will react with the diisocyanate during the first stage of the micro-encapsulation process when the stabilised biologically active compound is emulsified with the diisocyanate prior to introduction of the polyamine which will form the polyurea.

We have now discovered that certain tertiary polyamines can be used to stabilise certain behaviour modifying compounds which are susceptible to phtodegradation and that such stabilised compositions can be micro-encapsulated in polyurea microcapsules using conventional micro-encapsulation techniques.

According to one aspect of the present invention, there is provided a stabilised composition comprising a carbon-to-carbon unsaturated behaviour modifying compound as hereinafter defined and, as stabiliser therefor, a tertiary phenylene diamine of formula

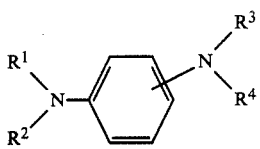

wherein R¹ represents an aromatic residue e.g. phenyl, R² represents H or an alkyl, alkenyl, cycloalkyl, cycloalkylalkyl, alkaryl, aralkyl, aryl, acyl, acyloxy or nitroso group and R³ and R⁴, which may be the same or different, each represents an alkyl, alkenyl, cycloalkyl, cycloalkylalkyl, alkaryl, aralkyl, aryl, acyl, acyloxy or nitroso group.

In the compositions of the present invention, it is preferred that the phenylene diamine be a para-phenylene diamine and that R¹ be an aromatic residue of up to 20, e.g. up to 15, carbon atoms, preferably a phenyl group. It is also preferred that at least one of R², R³ and R⁴ be an alkyl group and in the formula I, the alkyl groups, which may be straight or branched chained, preferably contain 1 to 20 carbon atoms. It is also preferred that the alkenyl groups contain 1 to 20 carbon atoms and that the cycloalkyl, cycloalkylalkyl, alkaryl, aralkyl or aryl groups contain up to 20 carbon atoms, particularly up to 15 carbon atoms. A compound of interest is the p-phenylene diamine where R¹ is phenyl, R² is H, R³ is methyl and R⁴ is 2-octyl.

When the stabilisers used in the present invention contain alkyl groups, these alkyl groups can be lower alkyl groups such as methyl, ethyl, propyl, isopropyl, or n-, iso-, sec- or tert-butyl or higher alkyl groups such as n- or isooctyl or n- or branched chain decyl, dodecyl or tetradecyl groups. When the stabilisers used in the present invention contain an acyl or acyloxy group, it is preferred that this will be an alkanoyl or an alkanoyloxy group where the alkanoyl group contains 1 to 20, particularly 1 to 6 carbon atoms, e.g. acetyl or propionyl, or higher groups such as oleoyl or palmitoyl. Although the acyl or acyloxy group will normally be a carboxylic acyl or acyloxy group of the type mentioned above, it is also possible to use acyl or acyloxy derivatives of sulphonic or phosphoric acids.

One preferred sub-class of stabiliser which can be used in the present invention are the compounds of formula I wherein R¹ represents phenyl, R² and R³ which may be the same or different, each represents a C₁ to C₂₀ alkyl, alkenyl or aralkyl group or a C₁-C₆ acyl or acyloxy group or a nitroso group and R⁴ represents a C₇ to C₂₀ alkyl group or a phenyl group. It is preferred that these compounds are paraphenylene diamines and typical examples of the C₁ to C₂₀ alkyl groups, which are preferably C₁ to C₆ alkyl groups, are the lower and higher alkyl groups mentioned above and typical C₇ to C₂₀ alkyl groups are the higher alkyl groups mentioned above. The alkenyl groups preferably contain up to 6 carbon atoms e.g. allyl. A particularly preferred compound of formula I for use in the present invention is the compound where R¹ is phenyl, R² and R³ are each methyl and R⁴ is 2-octyl as this compound is liquid at room temperature and consequently can be formulated into these compositions at higher concentrations than can the solid tertiary amines.

The stabilisers can be prepared by conventional methods, for example, by introducing groups R² and R³ into the corresponding secondary phenylene diamines which are commercially available compounds. For example, when it is desired to introduce alkyl groups R² and R³ into N-2-octyl-N'-phenyl-p-phenylene diamine, the secondary amine may be alkylated conventionally, e.g. by introducing the desired alkyl halide together with an appropriate base. Similarly, when it is desired to produce compounds including a nitroso or acyloxy group, these can be prepared by nitrosation or by acylation of the appropriate substituted hydroxy compound.

This invention is particularly designed for use with behaviour modifying compounds containing carbon-to-carbon unsaturation which are to be micro-encapsulated in polyurea micro-capsules. More specifically, the present invention is particularly applicable to formulation of the pheromone components of the Egyptian Cotton Leaf Worm (*Spodoptera littoralis*). This species is notorious in that the larvae are responsible for causing considerable damage to cotton crops and consequently, such damage could be reduced by an effective method of controlling this species utilising the pheromone to interfere with normal mating and so reduce larval infestations. It has been known for several years that three pheromones can be produced by this species, attractant components of formulae III and IIIa and an inhibitory component of formula IV

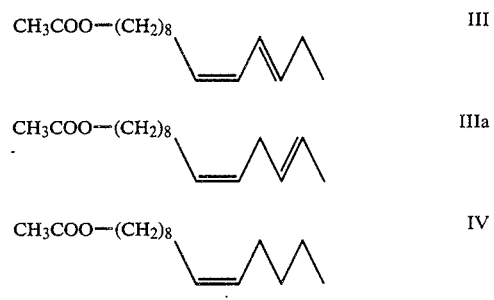

Other pheromones which can be formulated in accordance with the present invention are the female sex attractant of: the pink boll worm (*Pectinophera gossypiella*) which has been found to have two attractant components, compounds V and VI,

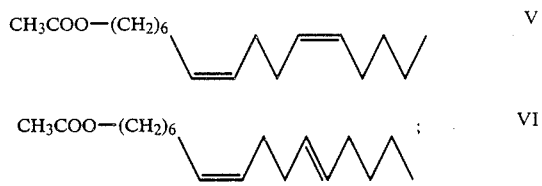

the red boll worm (*Diparopsis castanea*) which has three attractant components VIIa, VIIb and VIIc and an inhibitory component, VIII,

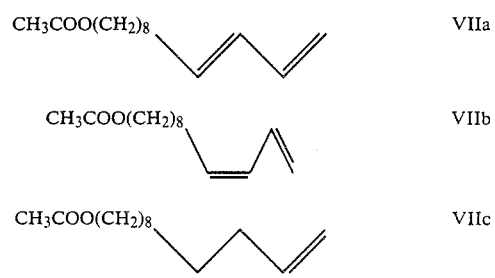

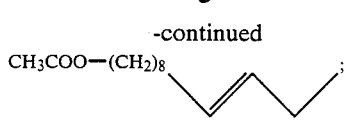

VIII the spruce bud worm (*Choristoneura fumiferana*) which has two components, IX and X,

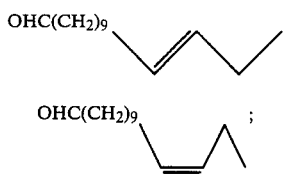

IX

X the corn ear worm (*Heliothis zea*) which has three unsaturated components XI–XIII,

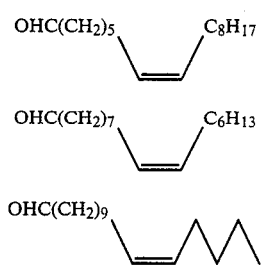

XI

XII

XIII and one saturated component, hexadecanal; and the tobacco bud worm (*Heliothis virescens*) which has all four components found in *Heliothis zea* and, in addition, a saturated component tetradecanal and two unsaturated components XIV and XV,

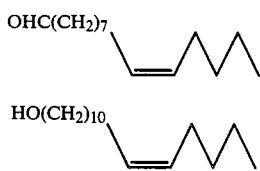

XIV

XV

The present invention is applicable not only to the formulation of pheromones but also to the formulation of so-called analogues of said pheromones for example, the compounds of formula XVI and XVII,

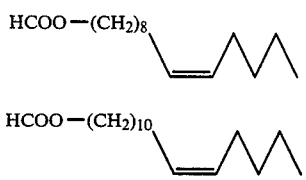

XVI

XVII which exhibit pheromone activity in relation to the rice stem borer (*Chilo suppressalis*) which itself has natural pheromones of formula XVIII and XIX,

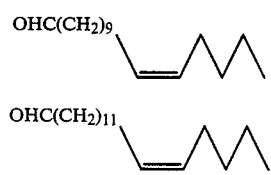

XVIII

XIX

The present invention may be used in relation not only to naturally produced but also to synthetically produced unsaturated behaviour modifying compounds. The above-identified pheromone components may be used singly or as mixtures in the compositions of the invention provided that at least one unsaturated behaviour modifying compound is present. Preferably the mixtures used correspond as closely as possible to the natural blend.

The term "behaviour modifying compound" as used in relation to this invention means:

(i) a compound secreted by a member of an insect species which can influence the behaviour of a member of the same or a different insect species;

(ii) a said compound (i) when prepared synthetically or a said compound (i) from a natural source other than a member of an insect species;

(iii) an analogue and/or isomer of a said compound (i), which analogue and/or isomer is prepared synthetically or is from a natural source other than a member of an insect species and itself can influence the behaviour of a member of an insect species.

In the above definition, "insect" is used in its broad popular sense. It includes within its scope members of the class Insecta, but is not restricted to these.

The term "analogue" in part (iii) of the above definition, means (a) homologues i.e. lower and higher unbranched or branched alkyl homologues of said compounds (i), (b) compounds having a greater or lesser number of sites of carbon-to-carbon unsaturation than said compounds (i), and/or (c) compounds containing a modification of the functional group of a said compound (i), e.g. in which a —CH$_2$CHO group in a said compound (i) is replaced by —OOCH, or in which a CHO group in a said compound (i) is replaced by CH$_3$, or in which the hydroxyl group in an alcohol compound (i) is replaced by an acyloxy group.

The term "isomer" in part (iii) of the above definition, means preferably compounds having one or more of the sites of carbon-to-carbon unsaturation in different positions from the positions in a said compound (i) and geometrical isomers i.e. isomers having different configuration at a carbon-to-carbon double bond or bonds compared with a said compound (i). Also preferred are structural isomers involving chain branching.

The relative proportions of the stabiliser and of the behaviour modifying compound in the compositions of the present invention are not particular critical and depend upon, inter alia, the extent of photoinstability of the active compound, the effectiveness of the stabilisers and the conditions under which the stabilised composition is to be used in the field. In general, it is found that the amine stabiliser should comprise about 10% to about 1,000% by weight of the behaviour modifying compound and our preliminary experiments have shown that very satisfactory results can be obtained using the two components of the composition in a 2:1 relationship to one another by weight. It is frequently found that the weight of stabiliser in the stabilised composition should be at least as great as that of the behaviour modifying compound in order to achieve optimum stabilisation and reduce, as far as it is possible, the number of occasions on which the stabilised composition needs to be applied to the locus to be protected. On the other hand, the use of excessive proportions of stabiliser is to be avoided as this is both unnecessarily expensive and also increases the volume of stabilised composition which needs to be used. Consequently, it will normally be found that the stabiliser comprises 50% to 500% by weight of the behaviour modifying compound.

In addition to containing the active compound and a stabiliser, the compositions of the present invention may also include further components which are designed to improve the physical or biological properties of the composition. For example, it has frequently been proposed to incorporate dark-coloured dyestuffs or pigments, the latter in the form of a dispersion, in the formulation of photodegradeable compounds in an attempt to minimise the photodegradation by masking the active photodegradeable compound from sunlight, and the compositions of the present invention may include dark coloured dyestuffs or pigments for this purpose. Typical dyestuffs that may be used include "Waxoline Blue" (colour index-solvent blue 36), "Waxoline Violet" (colour index-solvent violet 13), "Waxoline Black" (carbon black/solvent blue 36/solvent yellow 14/solvent red 24 mixture) or other similar solvent dyestuffs. A suitable pigment is a carbon black pigment dispersed in a hydrocarbon solvent. The composition may also include other stabilisers or surface active compounds in order to modify or improve the subsequent micro-encapsulation process and also other biologically active materials to supplement or potentiate the activity of the behaviour modifying compound. The composition may also include a solvent, e.g. an alkylbenzene, to solubilise the other ingredients and to improve the efficiency of the emulsification step during subsequent microencapsulation.

According to a further aspect of the present invention, there is provided a micro-encapsulated product comprising a suspension of polymeric microcapsules in an aqueous medium, the microcapsules containing an unsaturated behaviour modifying compound as hereinbefore defined and a tertiary phenylene diamine of formula I as defined above. The active composition contained inside the microcapsules may, for example, contain behaviour modifying compounds and stabilisers of the type specifically exemplified above.

The polymeric microcapsule which contains the active composition of the present invention may be any of the polymeric materials conventionally used for the micro-encapsulation of biologically active material. As mentioned above, the present invention is particularly designed for use in relation to polyurea microcapsules and, in accordance with a still further aspect of the present invention, there is provided a method of preparing a micro-encapsulated product which comprises emulsifying a diisocyanate, an unsaturated behaviour modifying compound and a tertiary phenylene diamine of formula I in an aqueous medium and subsequently introducing into the agitated emulsion a primary or secondary polyamine that will react with the diisocyanate to form a polyurea.

An alternative method of introducing the polyamine is to add it as a salt e.g. the hydrochloride, and then generate the free amine by adding a base. This may improve the stabilisation of behaviour modifying compounds that are aldehydes.

Although the present invention is particularly designed for use in relation to polyurea microcapsules, the principle of the present invention is applicable to the production of microcapsules from any polymeric material, although major advantages are to be secured when the polymeric material is one derived from a primary or secondary amino component. Other polymeric materials which can be used to formulate microcapsules of the present invention include polyamides, polyesters, polycarbonates and polyurethanes. The techniques generally employed for the production of the microcapsules are conventional interfacial condensation polymerisations, for example, as described in P. W. Morgan "Condensation Polymers by Interfacial and Solution Methods", published 1965 by Interscience. In general, the microcapsules are formed by a polycondensation reaction, e.g. between the diisocyanate and diamine in an aqueous phase under conditions of substantial agitation whereby the polymer is produced in the form of substantially spheroidal particles of diameter 1 to 100 microns and containing the stabilised composition of the invention. The ratio of the weight of the polymer-forming components (i.e. the monomers) to that of the material to be encapsulated will depend upon the nature of the microcapsule required and, particularly, on the wall thickness required which in turn controls the release rate of the stabilised composition of the invention, but the selection of appropriate wall thicknesses and appropriate microcapsule sizes is well within the competence of the art and reference may be made to any one of the numerous available publications relating to the micro-encapsulation art. However, a ratio of monomers to material to be encapsulated in the range of 0.1:1 to 3:1 has been found to be generally satisfactory.

According to one specific procedure, a solution of the behaviour modifying compound with solvent(s), antioxidant(s), UV absorber(s) etc. as required, together with the oil soluble monomer(s) is emulsified in water with the aid of suitable emulsifiers and high shear mixers. When the desired emulsion droplet size has been obtained, the water soluble monomer(s) are added and mixing continued until the reaction is complete. Any excess monomer or other acid acceptor is neutralised by the addition of acid, and anti-settling agents, wetting agents etc. can be added as desired. The emulsion droplet size largely controls the capsule size which is normally in the range 1–100 micron, preferably 1–5 micron, since the small microcapsules give better adhesion and retention when sprayed onto foliage. If desired, water soluble byproducts can be removed by filtration or centrifugation of the suspension and the micro-capsules can then be redispersed in an aqueous medium.

The rate of release of core material by diffusion through the capsule wall is controlled by the wall thickness i.e. the relative amounts of internal phase and polymer, and by the nature of the polymer i.e. its permeability.

Following micro-encapsulation of the stabilised composition of the invention, a sprayable liquid formulation is produced from which the biologically active material may be uniformly applied to the locus where it is desired to bring about behaviour control of the species involved. It is found that the micro-encapsulated product of the present invention exhibits the conventional storage stability properties of micro-encapsulated biologically active materials and can be applied e.g. by spraying, using techniques conventional for the application of micro-encapsulated materials. Consequently, in accordance with a still further feature of the present invention, there is provided a method of influencing the behaviour of a member of an insect species which comprises applying to a selected locus a stabilised composition according to the present invention or a micro-encapsulated stabilised composition according to the present invention. As will be readily appreciated, this aspect of the present invention is particularly applicable to the spraying of the stabilised composition or encapsulated stabilised composition on to growing crops so as to interfere with the normal mating of an insect species which, at at least certain stages of its development, acts as a pest on agricultural crops.

The following Examples are given to illustrate the present invention:

EXAMPLE 1

N,N'-Dimethyl-N-2-octyl-N'-phenyl-p-phenylene diamine 125 gm (2.5 mole) of 50% sodium hydride dispersion is washed free of mineral oil with petroleum ether and added to a solution of 296 gm (1 mole) of N-2-octyl-N'-phenyl-p-phenylenediamine (UOP 688) in 1500 ml dry dioxan. The slurry is stirred and heated at reflux for 2 hours and then allowed to cool. 75 ml (1.2 mole) methyl iodide is then added dropwise to the stirred slurry and there is an exothermic reaction. The mixture is then stirred and heated to reflux for 3 hours before cooling and adding a further 75 ml (1.2 mole) methyl iodide.

The cooled reaction mixture is quenched carefully with cold water. When all excess sodium hydride has been destroyed, 5 l of water is added and the phases separated. The lower, aqueous layer is washed twice with 250 ml petroleum ether, and the combined organic extracts are washed twice with 250 ml brine and dried over potassium hydroxide pellets. The solution is filtered through 100 gm neutral alumina and washed through with a further 200 ml petroleum ether. Solvents are removed on a rotary evaporator until the residue reaches constant weight (310 gm).

The product is a pale brown oil that darkens on exposure to light. It shows no reaction with toluene di-isocyanate after 16 hours at room temperature unlike UOP 688 which reacts exothermically with toluene di-isocyanate, and there is no N-H absorption in the infra-red spectrum.

The above reactions can be followed by thin layer chromatography on silica gel developed in chloroform containing 1% acetic acid, the spots being visualised with iodine vapour. Rf's: UOP 688 0.5 (purple spot), monomethyl 0.7 (pink), dimethyl 0.6 (blue).

EXAMPLE 2

The effectiveness of a range of stabilisers was tested by mixing 1 mg of tetradecyl acetate and 1 mg of (Z)-9-tetradecenyl acetate with the stabiliser in a glass pertri dish (5 cm diameter) so that the mixture formed a thin film over the base. This was then exposed horizontally on a roof for 24–48 hours, after which the residue was analysed by gas chromatography to determine the relative amounts of tetradecyl acetate and (Z)-9-tetradecenyl acetate. These compounds evaporate at similar rates, and so any difference between the amounts left is a measure of the degradation of the unsaturated compound. In the experiments described below, the result is expressed as the ratio of (Z)-9-tetradecenyl acetate:tetradecyl acetate, so that 1.00 indicates no degradation.

| Expt. | $R^1$ | Stabiliser $R^2$ | $R^3$ | $R^4$ | Amount of Stabiliser | Time | Result |
|---|---|---|---|---|---|---|---|
| A | | — | | | — | 24 hrs. | 0.05 |
| | | BHT | | | 1 mg | 24 hrs. | 0.13 |
| B | | (no stabiliser) | | | — | 10 hrs | 0.47 |
| | 2-octyl | H | H | 2-octyl | 0.2 mg | " | 0.62 |
| | phenyl | H | H | 2-octyl | 0.2 mg | " | 0.90 |
| C | | (no stabiliser) | | | — | 43 hrs | 0.06 |
| | phenyl | H | H | 2-octyl | 1 mg | " | 0.46 |
| | phenyl | H | H | phenyl | 1 mg | " | 0.58 |
| | CH$_3$ | CH$_3$ | CH$_3$ | CH$_3$ | 1 mg | " | 0.09 |
| | phenyl | CH$_3$ | CH$_3$ | 2-octyl | 1 mg | " | 0.13 |
| | phenyl | CH$_3$ | CH$_3$ | phenyl | 1 mg | " | 0.26 |
| D | | (no stabiliser) | | | — | 27 hrs | 0.28 |
| | phenyl | CH$_3$ | CH$_3$ | 2-octyl | 5 mg | " | 0.93 |
| | phenyl | H | H | 2-octyl | 1 mg | " | 0.75 |
| | phenyl | H | H | phenyl | 1 mg | " | 0.72 |
| E | phenyl | CH$_3$ | CH$_3$ | 2-octyl | 5 mg | 25 hrs | 0.92 |
| | " | " | " | " | " | 65 hrs | 0.78 |
| | " | " | " | " | " | 113 hrs | 0.60 |
| | | (no stabiliser) | | | — | 25 hrs | 0.14 |
| F | | (no stabiliser) | | | — | 28 hrs | 0.38 |
| | phenyl | H | H | 2-octyl | 1 mg | " | 0.80 |
| | | Waxoline black | | | 1 mg | " | 0.82 |

BHT=2,6-di-tert-butyl-4-methylphenol. The relationship of the amine groups in stabilisers for which $R^1$, $R^2$, $R^3$ and $R^4$ values are given in this Example is para in each case. N,N'-dimethyl-N-2-octyl-N'-phenyl-p-phenylene diamine (the product of Example 1) is an oil and hence can be formulated in the composition at a higher concentration than certain of the other N,N'-tetrasubstituted compounds.

EXAMPLE 3

Similarly to Example 2, the effectiveness of a range of stabilisers was tested by mixing 1 mg of tetradecyl acetate (14:Ac) and 1 mg of (Z)-9-tetradecenyl acetate (Z9-tda) with 1 mg of a stabiliser in a glass petri dish. This was exposed during daylight hours in London for a total of 60 hours, after which the residue was analysed by gas chromatography. The results are the mean of two replicates and comprise % of tetradecyl acetate (14:Ac) remaining (x%) and % of (Z)-9-tetradecenyl acetate (Z9-tda) remaining (y%). (100-x) then represents the percentage of 14:Ac lost by evaporation and (100-y) represents the percentage of Z9-tda lost by evaporation and degradation. % degradation is thus (x-y) and provides a comparative index of the effectiveness of each stabiliser:

| Stabiliser | | | | % remaining | | % |
|---|---|---|---|---|---|---|
| $R^1$ | $R^2$ | $R^3$ | $R^4$ | 14:Ac | Z9-tda | degradation |
| | | (no stabiliser)* | | 80.0 | 5.6 | 74.4 |
| phenyl | H | H | 2-octyl | 84.2 | 77.4 | 6.8 |
| " | CH$_3$ | CH$_3$ | " | 83.1 | 75.5 | 7.6 |
| " | C$_2$H$_5$ | C$_2$H$_5$ | " | 77.1 | 68.2 | 8.9 |
| " | nC$_{10}$H$_{21}$ | nC$_{10}$H$_{21}$ | " | 78.1 | 65.0 | 13.1 |
| " | benzyl | benzyl | " | 76.3 | 65.8 | 10.5 |
| " | —CH$_2$CH=CH$_2$ | —CH$_2$CH=CH$_2$ | " | 76.8 | 68.0 | 8.8 |
| " | —CH(CH$_3$)$_2$ | CH$_3$ | " | 79.7 | 69.0 | 10.7 |
| " | H | COCH$_3$ | " | 75.9 | 45.6 | 30.3 |

*plus 1 mg chlorinated wax "Cerechlor"

EXAMPLE 4

A micro-encapsulated product is prepared from the following composition:

|  | % w/v |  |
|---|---|---|
| (Z,E)-9,11-tetradecadienyl (Z9,E11-tdda) acetate or (Z)-9-tetradecenyl acetate (Z9-tda) | 2.0<br><br><br>2.0 | mixed together to form oil phase solution (1) |
| tetradecyl acetate | 2.0 | |
| Stabiliser A (N,N'—dimethyl-N—2-octyl-N'—phenyl-p-phenylene diamine) | 4.0 | |
| 'Waxoline Black' (TM) | 1.0 | |
| Toluene diisocyanate | 5.8 | |
| polyvinyl alcohol e.g. 'Polyviol M05/140' (TM) | 2.0 | mixed together to form aqueous phase solution (2) |
| water | 30.0 | |
| ethylene diamine | 1.0 | mixed together to form solution (3) |
| diethylene triamine | 2.5 | |
| water | 5.0 | |
| hydrochloric acid | to pH 7.5 | |
| hydroxyethylcellulose e.g. 'Natrosol 250L' (TM) | 0.5 | |
| water | to 100%. | |

Solution (1) is emulsified into solution (2) using a vortex shear mixer/emulsifier (e.g. a 'Silverson' TM) to give an oil/water emulsion of droplet size in the approximate range 1–5 micron. Solution (3) is then added quickly with stirring and a rapid condensation polymerisation reaction occurs at room temperature. Stirring is continued at a reduced rate for an hour and then the acid is added to lower the pH to 7.5, cooling if necessary. Finally the antisettling agent is added and the batch made up to volume with water. The resulting product is a free-flowing aqueous suspension of microcapsules of polyurea containing the acetate ester. The mean particle size of the microcapsules is in the range of 1 to 5 μm. Control products are prepared by a similar procedure but omitting Stabiliser A or by omitting both Stabiliser A and the dye.

A similar micro-encapsulated product was produced by replacing Z9,E11-tdda/Z9-tda with an identical amount of the attractant components of the pheromone of the pink boll worm i.e. (Z,E)-7,11-hexadecadienyl acetate (Z7,E11-hdda) and (Z,Z)-7,11-hexadecadienyl acetate (Z7,Z11-hdda) in a 1:1 ratio. In that case the saturated component (0.2%) was hexadecylacetate.

EXAMPLE 5

Micro-encapsulated formulations containing equal amounts of (Z)-9-tetradecenyl acetate (Z9-tda) and tetradecyl acetate (tda), with and without stabilisers, prepared as described in Example 4, were sprayed on to filter paper discs which were then exposed on a horizontal surface of a laboratory roof. Filter paper discs were removed at intervals and extracted with chloroform; the extracts were analysed quantitatively for the two acetates by gas chromatography. As the rates of evaporation for the two acetates would be similar, the difference between the amount of tda and Z9-tda remaining represented the amount of degradation of the unsaturated compound.

In experiments with formulations containing no tertiary phenylene diamine or dye as stabilisers, the Z9-tda typically disappeared within 6 days. After correcting for loss by evaporation, this indicated a loss of over 60% due to degradation.

In an experiment using a formulation containing N,N'-dimethyl-N-2-octyl-N'-phenyl-p-phenylene diamine, (diamine: Z9-tda 5:1 w/w), degradation was 13% after 13 days. With a similar formulation containing additionally the dye Waxoline Black (diamine:Z9-tda:dye, 5:1:0.5), degradation was 9% after 13 days.

In a further experiment using similar microcapsules but with different wall thicknesses containing the same diamine and dye the following results were obtained:

| Ratio diamine:Z9-tda:dye | Ratio monomers:internal phase (indication of wall thickness) | Ratio tetradecyl acetate: Z9-tda (at half life of tetradecyl acetate) |
|---|---|---|
| 5:1:0.5 | 0.6:1 | 1:0.84 |
|  | 1:1 | 1:0.88 |
| 2:1:0.5 | 1:1 | 1:0.76 |
|  | 1.5:1 | 1:0.71 |

These results show the better protection of the pheromones at the higher ratio of diamine.

EXAMPLE 6

In the field in Crete, a micro-encapsulated formulation of the type described in Example 4 and containing equal amounts of Z9-tda and tda stabilised by N,N'-dimethyl-N-2-octyl-N'-phenyl-p-phenylene diamine and Waxoline Black (diamine:Z9-tda:dye, 2:1:0.5) was sprayed on to filter papers attached to lucerne. The filter papers were sampled at intervals and analysed for residual Z9-tda and tda. After 14 days exposure the Z9-tda:tda ratio was unchanged, that is, there was no detectable degradation of the unsaturated compound. With unstabilised formulations sprayed under similar conditions there was typically no Z9-tda remaining after 3 to 6 days indicating degradation of 50% or more.

EXAMPLE 7

To measure the persistence of stabilised pheromones in microcapsules, the following formulations were sprayed onto filter papers which were stapled to the tops of cotton leaves in the field in Egypt.

The formulations were:
JF 7363—as Example 4 formulation with pheromone 9,11 tdda (70% ZE)
JF 7348—as Example 4 formulation with pheromone Z9 tda
JF 6956—as JF 7348 but with half wall thickness of microcapsules (by halving amount of toluene diisocyanate and adjusting amounts of polyamines incorporated)

Each formulation (10 ml) was mixed with 0.5 liter of water before being sprayed. The results were as follows

| | JF 7363 | | | |
|---|---|---|---|---|
| Day | % 14:Ac | % total 9,11-tdda | % ZE 9,11-tdda | total 9,11-tdda / 14-Ac |
| 0 | 100 | 100 | 100 | 0.56 |
| 1 | 95 | 66 | 29 | 0.39 |
| 2 | 78 | 38 | 16 | 0.27 |
| 3 | 68 | 24 | 10 | 0.19 |
| 4 | 72 | 21 | 8 | 0.17 |
| 5 | 58 | 9.7 | 3 | 0.10 |
| 6 | 51 | | | |
| 7 | 31 | | | |

-continued

| $t\frac{1}{2}$ (days) | 5.4 | 1.6 | 0.4 |
|---|---|---|---|

JF 6956

| Day | % 14:Ac | % Z9-tda | Z9-tda / 14:Ac |
|---|---|---|---|
| 0 | 100 | 100 | 0.75 |
| 1 | 87 | 88 | 0.77 |
| 2 | 64 | 65 | 0.77 |
| 3 | 82 | 86 | 0.80 |
| 4 | 77 | 80 | 0.78 |
| 5 | 64 | 62 | 0.73 |
| 6 | 62 | 56 | 0.67 |
| 7 | 51 | 44 | 0.65 |
| 8 | 36 | 30 | 0.71 |
| 10 | 30 | 24 | 0.67 |
| 12 | 18 | 12 | 0.57 |
| 18 | 10 | 6 | 0.46 |
| $t\frac{1}{2}$ (days) | 6.6 | 5.6 | |

JF 7348

| Day | % 14:Ac | % Z9-tda | Z9-tda / 14:Ac |
|---|---|---|---|
| 0 | 100 | 100 | 0.92 |
| 1 | 94 | 102 | 1.0 |
| 2 | 79 | 80 | 0.94 |
| 3 | 89 | 88 | 0.90 |
| 4 | 85 | 77 | 0.84 |
| 5 | 86 | 75 | 0.80 |
| 6 | 72 | 56 | 0.72 |
| 7 | 54 | 43 | 0.73 |
| 8 | 69 | 54 | 0.66 |
| 10 | 53 | 39 | 0.69 |
| 12 | 45 | 31 | 0.65 |
| 18 | 25 | 16 | 0.58 |
| $t\frac{1}{2}$ (days) | 8.5 | 6.6 | |

From the above results, it can be seen that the monoene Z9-tda was more persistent than the diene 9,11-tdda, disappearing at a rate similar to that of the saturated compound 14:Ac. This indicates that little of the loss of Z9-tda is due to degradation of the pheromone. Disappearance of both monoene and saturate was marginally faster for the thinner-walled capsules JF 6956 ($t\frac{1}{2}$ = 5.6 and 6.6 days respectively) than the thicker walled capsules JF 7348 ($t\frac{1}{2}$ = 6.6 and 8.5 days respectively). The diene 9,11 tdda had almost disappeared after 6 days exposure and the thermodynamic equilibrium mixture of the geometric isomers was reached in 2 days. No isomerisation of the monoene 9-tda was detected.

A similar experiment was carried out later, also in the field in Egypt, on formulation JF 7518 (as Example 4 formulation but with pheromone 7,11-hdda (1:1 ZE/ZZ) and saturated component (0.2%) hexadecylacetate) with the following results:

| Day | % 16:Ac | % 7,11-hdda | 7,11-hdda / 16:Ac |
|---|---|---|---|
| 0 | 100 | 100 | 6.1 |
| 2 | 74 | 72 | 5.9 |
| 4 | 57 | 56 | 5.9 |
| 5 | 72 | 48 | 4.0 |
| 7 | 63 | 31 | 3.0 |
| 9 | 37 | 14 | 2.5 |
| 11 | | 8 | 1.1 |
| 13 | | 4 | 0.9 |
| $t\frac{1}{2}$ (days) | 4.2 | | |

There was no detectable isomerisation after 13 days

EXAMPLE 8

Further experiments were carried out in Egypt to measure the persistance of stabilised pheromones in micro-capsules. The formulations studied were:

JF 7574 (control)—as Example 4 formulation with pheromone Z9-tda but only 1% w/v of tetradecylacetate (14:Ac), no stabiliser and no dye.

JF 7572 (control)—as JF 7574 but including 1% w/v black dye.

JF 7573—as JF 7572 but including 4% w/v stabiliser A.

| JF 7348(I) | see Example 7, | (I) taken to Egypt by land rover |
|---|---|---|
| JF 7348 (II) | | (II) taken to Egypt by air |

JF 7518—see Example 7

JF 7363—see Example 7

Each formulation (10 ml) was added to 50 ml water using a Mini-Ulvar sprayer and sprayed uniformly onto filter papers stapled in a regular pattern to square sheets of expanded polystyrene. Each sheet was split diagonally and the two halves fixed horizontally on a roof in Cairo so that the filter papers on one half faced upwards (exposed) and those on the other half faced downwards (shielded) about 1 m from the roof surface. At intervals, for each formulation, two randomly selected discs were removed from the exposed surface and two from the shielded surface and subsequently analysed.

Residual pheromone was extracted with chloroform containing a suitable internal standard for $\geq 12$ hours at room temperature and analysed quantitatively by gas chromatography.

In respect of both exposed and shielded samples, measurements were taken for JF 7574, JF 7572, JF 7573, and JF7348 (I) and (II) in respect of % 14:Ac and % Z9 tda and for JF 7363 in respect of % 14:Ac, % total 9,11-tdda and % ZE 9,11-tdda. Measurements for JF 7518 were taken of % 16:Ac and % 7,11-hdda (1:1 ZE/ZZ). From these, half lives for the pheromones in the active formulations were calculated as follows:

| | HALF LIFE (DAYS) | | | | | |
|---|---|---|---|---|---|---|
| | Field | | ROOF | | | |
| Formulation | (see Ex. 7) | | Exposed | | Shielded | |
| (JF) | sat | phero | sat | phero | sat | phero |
| 6956 | 6.6 | 5.6 | | | | |
| 7348(I) | 8.5 | 6.6 | 9.0 | 7.0 | >20 | >20 |
| 7348(II) | | | 8.0 | 6.7 | >20 | >20 |
| 7363 | 5.4 | 0.4* | 5.5 | <1* | >20 | 6* |
| | | 1.6+ | | 2.1+ | | 19+ |
| 7518 | | 4.2 | 5.8 | 4.0 | >20 | >20 |
| 7572 | | | 4.1 | 2.5 | >20 | >20 |
| 7573 | | | 3.0 | 2.2 | >20 | >20 |
| 7574 | | | 4.0 | 0.6 | >20 | 8.1 | sat = saturated component (14:Ac or 16:Ac)
phero = pheromone
*(ZE)-9,11-tdda
+total-9,11-tdda In the roof experiments, disappearance of the saturated component from exposed JF 7574 (no dye, no stabiliser) was less rapid ($t\frac{1}{2}$ = 4.0) than the disappearance of the pheromone ($t\frac{1}{2}$ = 0.6) due to light-induced degradation of the unsaturated component. The fact that the light-stable saturated component disappeared more quickly from exposed than from shielded samples is attributed to degradation of the microcapsule walls.

The dye present in JF 7572 reduces degradation of the unsaturated component while the degradation of the saturated component is similar to that in JF 7574 indicating that the dye has little effect on preventing microcapsule wall degradation.

Although the results with JF 7573 are satisfactory and roughly comparable with the JF 7572 results, greater half lives are obtainable when a stabiliser and a dye are present, c.f. JF 7348.

The results for JF 7518 and JF 7363 agree well with those for the same formulation sprayed on filter papers stapled to leaves at the tops of cotton plants in the field (see Example 7). It seems clear that the long-term persistence of the biological effects of each of these (see Examples 9 and 10) may depend to a considerable extent on shielding from sunlight by the plant either by spraying well down in the crop or by new growth effecting shielding.

Tests were also carried out in Brazil on a formulation JF 7546+JF 7518 (JF 7546 being identical to JF 7518 but with no saturated compound 16:Ac). The t½(days) for an unshielded sample was 2 days.

EXAMPLE 9

Formulations JF 7348 and JF 7363 (see Example 7) were sprayed onto cotton infested with *Spodoptera littoralis* in Egypt. These formulations contained, as active component, (Z,E)-9,11-tetradecadienyl acetate (Z9E11-tdda) and (Z)-9-tetradecenyl acetate (Z9-tda), respectively. The effect of the formulations in disrupting communication between male and female *S. littoralis* was monitored by comparison of catches of the male moth in traps baited with Z9,E11-tdda in areas sprayed with the formulations and in unsprayed control area. The percentage communication disruption on any one night is then the difference between the catch in the treated area and that in the unsprayed control area expressed as a percentage of the latter, complete communication disruption being indicated by 100%. The results were as follows:

| Treatment (g acetate ha$^{-1}$) | | Day | 0 | 1 | 2 | 3 | 4 | 5 | 6 | 7 | 8 | 9 | 10 | 11 | 12 | 13 | 14 |
|---|---|---|---|---|---|---|---|---|---|---|---|---|---|---|---|---|---|
| Z9-tda | 200 | $\bar{x}$ | 61.7 | 4.5 | 10.3 | 17.3 | 14.3 | 3.7 | 2.7 | 3.0 | 0 | 0 | 0 | 0 | — | — | — |
| formu- | | % | | 92.8 | 75.2 | 65.5 | 73.2 | 91.3 | 92.9 | 90.57 | 100 | 100 | 100 | 100 | | | |
| lation | 100 | $\bar{x}$ | 26.5 | 4.0 | 17.0 | 21.7 | 20.0 | 12.3 | 4.7 | 4.3 | 2.0 | 3.3 | 3.3 | 1.0 | — | — | — |
| | | % | | 93.6 | 59.1 | 56.8 | 62.5 | 71.1 | 87.6 | 86.4 | 90.1 | 87.3 | 90.4 | 95.0 | | | |
| | 50 | $\bar{x}$ | 57.5 | 2.0 | 4.7 | 6.7 | 5.7 | 3.3 | 4.0 | 2.7 | 2.7 | 1.0 | 2.0 | 8.0 | | | |
| | | % | | 96.8 | 88.7 | 86.7 | 89.3 | 92.3 | 89.5 | 91.5 | 86.6 | 96.2 | 94.2 | 59.6 | | | |
| Z9E11-tdda | 80 | $\bar{x}$ | 60.6 | 0.3 | 1.0 | 0.3 | 0.7 | 0.7 | 1.3 | 0 | 0 | 0 | 0.7 | 0 | 0.32 | 1.0 | 1.0 |
| formu- | | % | | 99.5 | 97.6 | 99.4 | 98.7 | 98.4 | 96.6 | 100 | 100 | 100 | 98.0 | 100 | 98.9 | 97.7 | 91.9 |
| lation | 40 | $\bar{x}$ | 41.7 | 0.3 | 2.3 | 0 | 0.3 | 4.0 | 6.3 | 6.3 | 0 | 2.7 | — | 0.3 | 0 | 0.7 | |
| | | % | | 99.5 | 94.5 | 100 | 99.4 | 90.6 | 83.4 | 80.1 | 100 | 89.6 | 98.0 | — | 98.9 | 100 | 94.4 |
| | 20 | $\bar{x}$ | 43.7 | 3.7 | 1.3 | 21.0 | 28.0 | 27.3 | 10.7 | 8.3 | 1.0 | 7.7 | 7.7 | 2.3 | 6.0 | 8.7 | 4.3 |
| | | % | | 94.1 | 96.9 | 58.2 | 47.6 | 35.9 | 71.8 | 73.7 | 95.0 | 70.4 | 77.6 | 88.4 | 78.9 | 80.1 | 65.3 |
| Controls | | $\bar{x}$ | 62.4 | 62.2 | 41.6 | 50.2 | 53.4 | 42.6 | 38.0 | 31.6 | 20.2 | 26.0 | 34.4 | 19.8 | 28.4 | 43.8 | 12.4 |

$\bar{x}$ = mean number of *S.littoralis* male moths caught per trap per day

% = % disruption in terms of numbers caught relative to controls.Plot size for this experiment was 0.01 ha.

In a second experiment the Z9E11-tdda formulation was sprayed at twolevels on plots of two different sizes. The results were as follows:-

| Rate (g acetate ha$^{-1}$) | Plot size ha | | Day 0 | 2 | 3 | 5 | 8 | 10 | 12 | 14 | 16 | 18 | 21 |
|---|---|---|---|---|---|---|---|---|---|---|---|---|---|
| 19 | 0.01 | $\bar{x}$ | 2.0 | 0.3 | 0.3 | 0 | 0.4 | 2.7 | 2.7 | 4.8 | 9.2 | 7.3 | 11.8 |
| | | % | | 62.5 | — | — | 96.3 | 92.8 | 94.1 | 82.2 | 87.7 | 76.6 | 63.5 |
| 38 | 0.01 | $\bar{x}$ | 0.7 | 0 | 0 | 0 | 2.0 | 7.3 | 10.8 | 11.0 | 11.8 | 8.0 | 7.1 |
| | | % | | 100 | 100 | — | 81.5 | 80.6 | 7.5 | 59.1 | 84.2 | 73.7 | 78.0 |
| 19 | 0.1 | $\bar{x}$ | 0.3 | 0 | 0 | 0 | 0.6 | 1.5 | 2.0 | 2.7 | 2.7 | 2.8 | 3.6 |
| | | % | | 100 | 100 | — | 94.4 | 96.0 | 95.6 | 90.0 | 96.4 | 90.8 | 88.9 |
| 38 | 0.1 | $\bar{x}$ | 0.7 | 0 | 0 | 0 | 1.0 | 1.5 | 1.8 | 3.0 | 3.0 | 2.0 | 3.9 |
| | | % | | 100 | 100 | — | 90.7 | 96.0 | 96.1 | 88.8 | 96.0 | 93.4 | 87.9 |
| Control | | $\bar{x}$ | 0.3 | 0.8 | 0.3 | 0 | 10.8 | 37.7 | 45.9 | 26.9 | 74.5 | 30.4 | 32.3 |

EXAMPLE 10

Formulation JF 7518 (see Example 7) was sprayed onto cotton infested with *Pectinophera gossypiella* in Egypt. This formulation contained, as active component, 7,11-hexadecadienyl acetate (7,11-hdda-1:1 ZE/ZZ). The effect was monitored in the same way as in Example 9, the traps being baited in this case with the compound sprayed (7,11-hdda). Results were as follows for 0.01 ha plots:

| | CONTROL | MICROCAPS 2.5 g/ha | | 5 g/ha | | 10 g/ha | |
|---|---|---|---|---|---|---|---|
| DAY | $\bar{x}$ | $\bar{x}$ | % | $\bar{x}$ | % | $\bar{x}$ | % |
| | 2.8 | 4.5 | | 0.2 | | 2.3 | |
| | 6.4 | 7.7 | | 3.0 | | 8.3 | |
| | 3.2 | 3.7 | | 0.3 | | 5.3 | |
| | 2.4 | 6.7 | | 0.3 | | 4.3 | |
| 0 | 3.0 | 9.3 | | 3.7 | | 5.0 | |
| 1 | 0.7 | 0 | 100 | 0 | 100 | 0 | 100 |
| 2 | 0.5 | 0 | 100 | 0 | 100 | 0 | 100 |
| 3 | 0.5 | 1.0 | | 0 | 100 | 0 | 100 |
| 4 | 10.7 | 1.3 | 88 | 0 | 100 | 0.3 | 97 |
| 5 | 4.8 | 1.7 | 65 | 0 | 100 | 0 | 100 |
| 6 | 7.0 | 1.0 | 86 | 2.0 | 71 | 0.7 | 90 |
| 7 | 5.5 | 2.0 | 64 | 0.3 | 95 | 0.3 | 95 |
| 8 | 7.2 | 2.7 | 63 | 1.0 | 86 | 1.0 | 86 |
| 9 | 7.7 | 0.7 | 91 | 0.7 | 91 | 1.3 | 83 |
| 10 | 6.2 | 4.0 | 35 | 1.0 | 84 | 3.0 | 52 |
| 11 | 15.7 | 3.3 | 79 | 0 | 100 | 1.0 | 94 |
| 12 | 8.5 | 3.3 | 61 | 1.7 | 80 | 1.3 | 85 |
| 13 | 5.3 | 9.3 | | 0.7 | 87 | 4.3 | 19 |
| 14 | 17.0 | 10.0 | 41 | 1.3 | 92 | 3.7 | 78 |
| 15 | | | | | | | |
| 16 | 16.7 | 5.2 | 69 | 0.7 | 96 | 3.8 | 77 |
| 17 | | | | | | | |
| 18 | 32.1 | 9.0 | 72 | 3.0 | 91 | 4.0 | 88 |
| 19 | | | | | | | |
| 20 | 26.8 | 9.2 | 66 | 3.7 | 86 | 2.0 | 93 |
| 21 | | | | | | | |
| 22 | 18.0 | 16.7 | 7 | 2.7 | 85 | 6.7 | 63 |

-continued

| | CONTROL | MICROCAPS | | | | | |
| | | 2.5 g/ha | | 5 g/ha | | 10 g/ha | |
| DAY | x̄ | x̄ | % | x̄ | % | x̄ | % |
|---|---|---|---|---|---|---|---|
| 23 | 24.2 | 17.0 | 30 | 3.0 | 88 | 7.7 | 68 |
| 24 | 36.5 | 11.7 | 68 | 11.0 | 70 | 19.7 | 46 |
| 25 | 36.7 | 26.3 | 28 | 7.0 | 81 | 12.0 | 67 |
| 26 | 32.0 | 33.0 | | 6.0 | 81 | 11.3 | 69 |
| 27 | | | | | | | |
| 28 | 28.9 | 36.0 | | 9.2 | 68 | 10.5 | 64 | x̄ = mean no. of *P. gossypiella* male moths caught per trap per day
% = % disruption in terms of numbers caught relative to controls

| | CONTROL | MICROCAPS | | | |
| | | 20 g/ha | | 40 g/ha | |
| Day | x̄ | x̄ | % | x̄ | % |
|---|---|---|---|---|---|
| | 13.7 | 1.8 | | 18.7 | |
| | 21.7 | 12.2 | | 32.7 | |
| | 10.8 | 7.5 | | 40.0 | |
| | 47.0 | 11.3 | | 30.7 | |
| 0 | 24.0 | 8.3 | | 30.7 | |
| 1 | 22.3 | 0 | 100 | 0 | 100 |
| 2 | 17.0 | 0 | 100 | 0 | 100 |
| 3 | 44.0 | 0 | 100 | 0 | 100 |
| 4 | 37.3 | 0 | 100 | 0 | 100 |
| 5 | 34.0 | 0 | 100 | 0 | 100 |
| 6 | 29.0 | 0.3 | 99 | 0.3 | 99 |
| 7 | 22.0 | 0 | 100 | 0 | 100 |
| 8 | 18.0 | 0.3 | 98 | 0.3 | 98 |
| 9 | 21.0 | 0 | 100 | 0 | 100 |
| 10 | 63.3 | 0 | 100 | 0.3 | 99.5 |
| 11 | 39.7 | 0 | 100 | 0 | 100 |
| 12 | 29.0 | 0 | 100 | 0.3 | 99 |
| 13 | 66.7 | 0.3 | 99.6 | 0 | 100 |
| 14 | 35.0 | 0.3 | 99 | 0 | 100 |
| 15 | 38.7 | 0 | 100 | 0.3 | 99 |
| 16 | 97.3 | 0.7 | 99 | 0 | 100 |
| 17 | 66.0 | 0 | 100 | 0 | 100 |
| 18 | 88.0 | 0 | 100 | 0 | 100 |
| 19 | 71.0 | 0 | 100 | 0 | 100 |
| 20 | 45.0 | 0 | 100 | 0 | 100 |
| 21 | 78.3 | 0 | 100 | 0 | 100 |
| 22 | 118.0 | 1.0 | 99.2 | 0 | 100 |
| 23 | 63.7 | 0 | 100 | 0 | 100 |
| 24 | 65.3 | 0 | 100 | 1.0 | 98.5 |
| 25 | 85.6 | 0 | 100 | 0.4 | 99.5 |
| 26 | 85.6 | 0 | 100 | 0.4 | 99.5 |
| 27 | 177.3 | 0 | 100 | 0 | 0 |
| 28 | 115.0 | 1.0 | 99.1 | 0.3 | 99.7 | x̄ = mean no. of *P. gossypiella* male moths caught per trap per day
% = % disruption in terms of numbers caught relative to controls.

From these results, it can be seen that the microcapsules at 10 g/ha maintained ≧90% disruption for 7 days, while at levels of 20 g/ha and 40 g/ha virtually complete disruption was caused for the 28 days of the experiment—≧98% for the microcapsules at both levels.

Similar tests on the JF 7546+JF 7518 formulation in Brazil (c.f. Example 8) at 16 g/ha showed that this maintained >90% disruption for 9 days.

We claim:

1. A micro-encapsulated product comprising a suspension of microcapsules in an aqueous medium, the microcapsules, per se, being unable to fully protect photodegradeable active components contained in said microcapsules against photodegradation, and said microcapsules being of a polymeric material selected from the group consisting of polyamides, polyesters, polycarbonates, polyureas, polyurethanes and synthetic polymers having a polymerization component which is reactive with a primary or secondary amine, and which microcapsules encapsulate a composition comprising a photodegradeable carbon-to-carbon unsaturated insect behaviour modifying compound which compound is selected from the group consisting of (a) a compound secreted by a member of an insect species which can influence the behaviour of a member of the same or a different insect species, (b) a synthetic compound (a), (c) compound (a) derived from a natural source other than a member of an insect species, (d) an analogue of compound (a), (e) an isomer of compound (a), and mixtures thereof, and wherein said analogue and said isomer are synthetically prepared or are derived from a natural source other than a member of an insect species and themself can influence the behaviour of a member of an insect species, and, as stabiliser therefor, a tertiary phenylene diamine of the formula

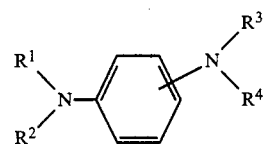

wherein $R^1$ represents an aromatic residue containing 6 to 20 carbon atoms, $R^2$ represents H or an alkyl, alkenyl, cycloalkyl, cycloalkylalkyl, alkaryl, aralkyl, aryl, acyl or acyloxy group, said groups containing 1 to 20 carbon atoms, or a nitroso group and $R^3$ and $R^4$, which may be the same or different, each represents an alkyl, alkenyl, cycloalkyl, cycloalkylalkyl, alkaryl, aralkyl, aryl, acyl or acyloxy group, said groups containing 1 to 20 carbon atoms, or a nitroso group, the weight of the stabiliser in the stabilized composition being from 10% to 1000% of the behaviour modifying compound.

2. The product according to claim 1, wherein, in the stabiliser of formula I, $R^1$ represents a phenyl, $R^2$ and $R^3$ which may be the same or different, each represents a $C_1$ to $C_{20}$ alkyl, alkenyl or aralkyl group or a $C_1$ to $C_6$ acyl or acyloxy group or a nitroso group and $R_4$ represents a $C_7$ to $C_{20}$ alkyl group or a phenyl group.

3. The product according to claim 1, wherein the stabiliser is an N,N'-dialkyl-N-2-octyl-N'-phenyl-p-phenylene diamine, an N-alkyl-N-2-octyl-N'-phenyl-p-phenylene diamine, and N,N'-dialkenyl-N-2-octyl-N'-phenyl-p-phenylene diamine or an N,N'-diaralkyl-N-2-octyl-N'-phenyl-p-phenylene diamine.

4. The product according to claim 3 wherein the stabiliser is N,N'-dimethyl-N-2-octyl-N'-phenyl-p-phenylene diamine.

5. The product according to claim 1 wherein the stabiliser comprises 50 to 500% by weight of the behaviour modifying compound.

6. The product according to claim 1 wherein the behaviour modifying compound is: (Z,E)-9,11-tetradecadienyl acetate, (Z,E)-9,12-tetradecadienyl acetate, (Z)-9-tetradecenyl acetate, (Z,E)- or (Z,Z)-7,11-hexadecadienyl acetate, (E)- or (Z)-9,11-dodecadienyl acetate, 11-dodecenyl acetate, (E)-9-dodecenyl acetate (E)- or (Z)-11-tetradecenal, (Z)-7-hexadecenal, (Z)-9-hexadecenal, (Z)-11-hexadecenal, (Z)-9-tetradecenal, (Z)-9-tetradecenyl formate or (Z)-11-hexadecenyl formate or a mixture of any of these.

7. The product according to claim 1 which also contains a dark-coloured dyestuff or pigment.

8. The product according to claim 1 wherein the polymeric material of the microcapsule is a polyurea.

9. A method of influencing the behaviour of a member of an insect species which comprises applying to a selected locus an effective amount of micro-encapsulated product as claimed in claim 1.

10. The product according to claim 1, wherein the behaviour modifying compound is a pheromone.

11. The product according to claim 1, wherein the polymeric material is a synthetic polymer having a polymerization component which is reactive with a primary or secondary amine.

12. The product according to claim 1, wherein the polymeric material is selected from the group consisting of polyamides, polyesters, polycarbonates, polyureas and polyurethanes.

13. The product according to claim 12, wherein the polymeric material is a polyurea.

* * * * *